(12) United States Patent
Eil et al.

(10) Patent No.: US 10,970,813 B2
(45) Date of Patent: Apr. 6, 2021

(54) SHAKING IMAGE FOR REGISTRATION VERIFICATION

(71) Applicant: ALCON INC., Fribourg (CH)

(72) Inventors: Martin Eil, Berlin (DE); Tobias Jura Rapoport, Berlin (DE)

(73) Assignee: Alcon Inc.

( * ) Notice: Subject to any disclaimer, the term of this patent is extended or adjusted under 35 U.S.C. 154(b) by 73 days.

(21) Appl. No.: 16/385,936

(22) Filed: Apr. 16, 2019

(65) Prior Publication Data

US 2020/0005429 A1    Jan. 2, 2020

Related U.S. Application Data

(60) Provisional application No. 62/693,169, filed on Jul. 2, 2018.

(51) Int. Cl.

| | |
|---|---|
| *G06T 3/00* | (2006.01) |
| *A61B 90/20* | (2016.01) |
| *A61B 90/00* | (2016.01) |
| *G06T 7/33* | (2017.01) |
| *A61F 9/007* | (2006.01) |
| *G06T 3/60* | (2006.01) |

(52) U.S. Cl.
CPC ............ *G06T 3/0068* (2013.01); *A61B 90/20* (2016.02); *A61B 90/361* (2016.02); *A61F 9/007* (2013.01); *G06T 3/60* (2013.01); *G06T 7/337* (2017.01); *A61B 2090/365* (2016.02); *A61B 2090/373* (2016.02); *G06T 2207/10056* (2013.01); *G06T 2207/20092* (2013.01); *G06T 2207/30041* (2013.01)

(58) Field of Classification Search
CPC ......... G06T 3/0068; G06T 7/337; G06T 3/60; G06T 2207/10056; G06T 2207/20092; G06T 2207/30041; A61B 90/20; A61B 90/361; A61B 2090/365; A61B 2090/373; A61B 3/13; A61B 2017/00725; A61B 2090/364; A61B 90/36; A61B 34/20; A61B 3/152; A61B 3/0025; A61B 3/132; A61F 9/007

See application file for complete search history.

(56) References Cited

U.S. PATENT DOCUMENTS

| | | |
|---|---|---|
| 2010/0094262 A1 | 4/2010 | Tripathi |
| 2012/0022408 A1* | 1/2012 | Hubschman ........... A61B 90/36 600/587 |

(Continued)

FOREIGN PATENT DOCUMENTS

| | | |
|---|---|---|
| EP | 1800636 A1 | 6/2007 |
| WO | WO2017191487 A1 | 11/2017 |

OTHER PUBLICATIONS

Carl Zeiss; Zeiss Cataract Suite markerless (Brochure) 2016 by Carl Zeiss Meditec AG (https://www.zeiss.com/meditec/us/products/ophthalmology-optometry/cataract/zeiss-cataract-suite-markerless.html).

(Continued)

*Primary Examiner* — Christopher M Brandt

(57) ABSTRACT

A method and system are described that allow a user to verify a registration proposal during an image-guided ophthalmic surgery. The system configured to perform the method has a processor and a non-transitory computer-readable medium accessible to the processor containing instructions executable by the processor to perform the method.

20 Claims, 3 Drawing Sheets

(56) References Cited

U.S. PATENT DOCUMENTS

| | | | |
|---|---|---|---|
| 2016/0100909 A1* | 4/2016 | Wollowick | G06T 7/33 600/424 |
| 2016/0346047 A1* | 12/2016 | Tripathi | A61B 90/20 |
| 2016/0353022 A1* | 12/2016 | Mueller | F16M 13/027 |
| 2016/0364878 A1* | 12/2016 | Guo | G06T 7/11 |
| 2017/0164829 A1* | 6/2017 | Awdeh | G02B 21/244 |
| 2018/0049840 A1* | 2/2018 | Awdeh | A61B 90/20 |
| 2019/0151024 A1* | 5/2019 | Abraham | A61F 9/008 |

OTHER PUBLICATIONS

Verion Image Guided System (obtained online Jul. 1, 2019 from: https://www.myalcon.com/professional/surgical-diagnostics/verion/improved-workflow).

\* cited by examiner

SHAKING IMAGE FOR REGISTRATION VERIFICATION

BACKGROUND

The present disclosure relates to ophthalmic surgery, and more specifically, to a method and system configured to allow a user to verify a registration proposal during an image-guided ophthalmic surgery.

In ophthalmology, ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Image-guided surgery systems may be used for surgical procedures that are based on pre-operative planning. During image-guided ophthalmic surgery, a pre-operative image, such as a diagnostic image, of a patient's eye may be used as a reference image for guiding an ophthalmic surgeon to perform a surgical procedure on the patient's eye. The pre-operative image may be considered a reference image and may include markings indicating coordinates for guiding an ophthalmic surgeon, such a marking indicating a location within a structure of the patient's eye that is a target for a surgical procedure.

Typically, for image-guided ophthalmic surgery, a registration step is performed wherein a pre-operative reference image of a patient's eye is aligned with an intra-operative image of the patient's eye. The alignment is performed to match the location of features of the pre-operative image of a patient's eye, such as scleral blood vessels, iris features, and limbus, with the location of the same features in the intra-operative image of the patient's eye. The registration step may include a rotation of the pre-operative image relative to the intra-operative image, which may be referred to as a registration angle. Various ophthalmic surgery systems employ computer processors that execute algorithms for performing the registration step. The result of the registration step performed by the system may be referred to as a proposed registration, or registration proposal, which includes a proposed registration angle. Typically, following the proposed registration, an ophthalmic surgeon performs a verification step, wherein the ophthalmic surgeon checks the proposed registration. Existing approaches for verifying the proposed registration present challenges to the ophthalmic surgeon. For example, this often requires manual intervention to assess whether the proposed registration angle represents an optimal registration angle. However, improvements in the process whereby the ophthalmic surgeon verifies the proposed registration remain challenging.

SUMMARY

The present disclosure provides a system configured for verifying, by a user, a proposed registration during ophthalmic surgery. The system includes a processor and a non-transitory computer-readable medium accessible to the processor containing instructions executable by the processor for: acquiring, from a photosensor, an intra-operative image of a patient's eye under magnification by a microscope; retrieving, from a non-transitory computer-readable medium, a pre-operative reference image of the patient's eye, wherein the limbus of the pre-operative image of the patient's eye has a center; performing a registration process to provide a proposed registration of the pre-operative reference image of the patient's eye and the intra-operative image of the patient's eye; overlaying the pre-operative reference image and the intra-operative image to provide a merged image having the proposed registration, wherein the merged image is viewable by the user; adjusting the transparency of at least one of the pre-operative reference image and the intra-operative image, so that the pre-operative reference image and the intra-operative image are simultaneously viewable in the merged image by the user; and rotating the viewable pre-operative reference image relative to the viewable intra-operative image in the viewable merged image, wherein the rotating is centered on the center of the limbus of the patient's eye in the pre-operative reference image. The system is thereby configured to allow the user to verify a proposed registration during ophthalmic surgery.

In any of the disclosed implementations, the system and method may further include the following details, which may be combined with the method and system, and with one another, in any combinations unless clearly mutually exclusive:

i) the transparency may be selected from between about 1-10%, 10-20%, 20-30%, 30-40%, 40-50%, 50-60%, 60-70%, 70-80%, 80-90%, and 90-99%;

ii) the transparency may be about 50%;

iii) the rotating may be clockwise;

iv) the rotating may be anticlockwise;

v) the rotating may include at least one clockwise and at least one anticlockwise rotation, wherein the clockwise and the anticlockwise rotations alternate;

vi) the rotation may be repeated from about 1 to 20 times;

vii) the rotation may be repeated with a frequency of between 1-10 Hz;

viii) the rotation may have an angle of between about 1°-10°;

ix) the angle may be about 5°;

x) the rotating may include a series having a plurality of viewable alternating clockwise and anticlockwise rotations wherein: the series has a first viewable rotation having a first angle; and following the first viewable rotation, each successive viewable rotation of the series has a smaller angle;

xi) the plurality of viewable rotations may include about 10 rotations;

xii) the first angle may be about 10°;

xiii) the angle of each successive viewable rotation may decrease by about 1°;

xiv) following the series, the proposed registration may be viewable;

xv) the system and method may further include one or more of the performing, overlaying, adjusting, and rotating steps;

xvi) the microscope may include oculars, and the non-transitory computer-readable medium accessible to the processor may contain instructions executable by the processor for displaying the viewable merged image via the oculars;

xvii) the system may include a display, and the non-transitory computer-readable medium accessible to the processor may contain instructions executable by the processor for displaying the viewable merged image on the display;

xviii) the overlaying, adjusting, and rotating may be initiated by the processor executing instructions contained in the non-transitory computer-readable medium; and xix) the overlaying, adjusting, and rotating may be initiated by the user.

BRIEF DESCRIPTION OF THE DRAWINGS

For a more complete understanding of the present disclosure, reference is now made to the following description, taken in conjunction with the accompanying drawings, which are exemplary and not drawn to scale, and in which.

DETAILED DESCRIPTION

Figure 1:
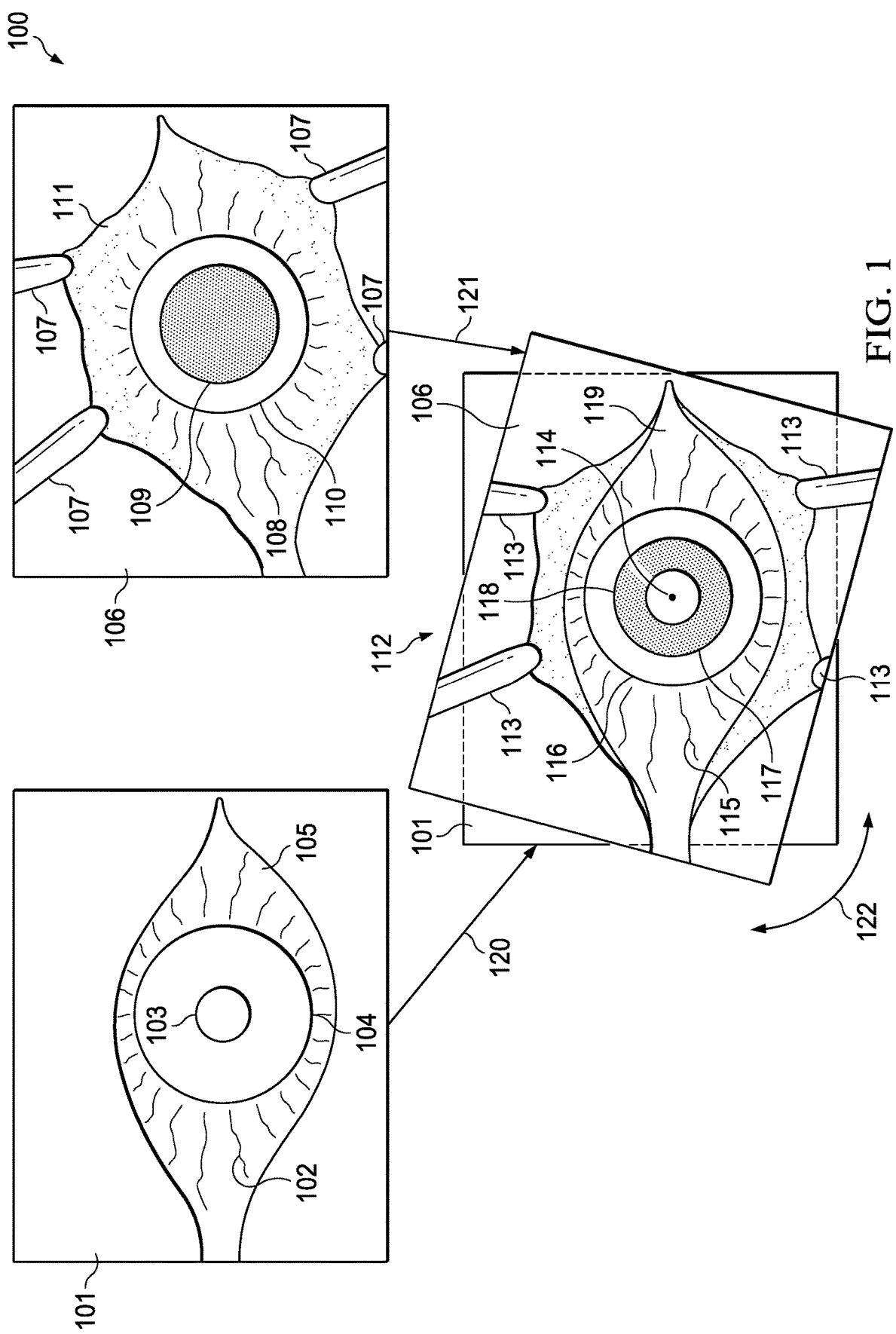
FIG. 1 is an exemplary schematic illustration of a pre-operative reference image of an eye, an intra-operative image of the patient's eye, and a merged image of the pre-operative reference image and the intra-operative image, wherein the merged image has a proposed registration, illustrating an exemplary method of verifying a proposed registration during ophthalmic surgery.

In the following description, details are set forth by way of example to facilitate discussion of the disclosed subject matter. It should be apparent to a person of ordinary skill in the art, however, that the disclosed implementations are exemplary and not exhaustive of all possible implementations.

The present disclosure relates to ophthalmic surgery, and more specifically, to a method to allow a user to verify a proposed registration during an image-guided ophthalmic surgery, and a system configured to perform the method.

Ophthalmic surgery is performed on the eye and accessory visual structures. For example, vitreoretinal surgery encompasses various delicate procedures involving internal portions of the eye, such as the vitreous humor and the retina. The retina is a light-sensitive area that includes the macula, which is made up of light-sensitive cells that provide sharp, detailed vision. The vitreous humor of the eye is a clear gel that fills the space between the retina and the lens. The retina, the macula, and the vitreous body can all be subject to various diseases and conditions that can lead to blindness or vision loss and may require the attention of a vitreoretinal surgeon.

Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

Ophthalmic surgery often involves removal of eye tissue. For example, cataract surgery generally requires the removal and replacement of the lens. An artificial lens or intraocular lens implant can then be implanted within the eye to restore or improve the eyesight of the patient. Other procedures may also involve the removal of lens tissue and/or other types of eye tissue.

There are a number of procedures and devices that have been developed for the removal of eye tissue. For example, phacoemulsification is a widely used method for removal of diseased or damaged lens tissue. The phacoemulsification process generally involves insertion of a probe through a small corneal incision to break apart and remove the lens in cataract surgery.

In phacoemulsification, one or more incisions are generally made in the eye to allow the introduction of surgical instruments. The surgeon then removes the anterior face of the capsule that contains the lens inside the eye. An ultrasonic handpiece, where the tip vibrates at ultrasonic frequency, is generally used to sculpt and emulsify the cataract. After removal of the cataract, the posterior capsule is generally still intact and an intraocular lens implant (IOL) can be placed into the remaining lens capsule.

During ophthalmic surgery, because of the small size and delicate nature of the eye structures, surgeons typically use a microscope to magnify visualization of a patient's eye or a part of the eye that is being operated on.

Ophthalmic surgeons may use eyepieces, otherwise known as oculars, to view the eye or part thereof that is being magnified by the microscope. During ophthalmic surgery, stereo microscopes having two eyepieces viewable by both eyes simultaneously for binocular view are typically used. As an alternative to using eyepieces, or in addition, during ophthalmic surgery, developments in digital microscopy have allowed both real-time intra-operative and stored pre-operative images of the eye or part thereof that is magnified by the microscope to be displayed on a screen viewable by the surgeon.

Ophthalmic surgery visualization platforms utilizing digital microscopy and display screens applicable to the method and systems described herein generally include at least one high resolution photosensor such as a camera or charge coupled device (CCD) which is capable of receiving and acquiring one or more optical views of an eye under magnification by a microscope. Those skilled in the art will appreciate that receiving light in visible wavelengths in addition to wavelengths outside of the wavelengths of normal visible light is also within the scope of the present invention. In general, the high resolution photosensor then transmits a resultant image signal which is transmitted, via a processor executing instructions contained in a non-transitory computer readable medium, to a high-resolution display.

Image-guided surgery systems may be used for surgical procedures that are based on pre-operative planning. During image-guided ophthalmic surgery, a pre-operative image, such as a diagnostic image, of a patient's eye may be used as a reference image for guiding an ophthalmic surgeon to perform a surgical procedure on the patient's eye. The pre-operative image may be considered a reference image and may include markings indicating coordinates for guiding an ophthalmic surgeon, such markings indicating a location within a structure of the patient's eye that is a target for a surgical procedure.

The term "display" as used herein refer to any device capable of displaying a still or video image. Preferably, the displays of the present disclosure display high definition (HD) still images and video images or videos which provide a surgeon with a greater level of detail than a standard definition (SD) signal. In some implementations, the displays present such HD stills and images in three dimensions (3D). Exemplary displays include HD monitors, cathode ray tubes, projection screens, liquid crystal displays, plasma display panels, light emitting diodes (LED) or organic LED (OLED), 3D equivalents thereof and the like. 3D HD holographic display systems are considered to be within the scope of the present disclosure.

The visualization platforms described herein include at least one high resolution photosensor. A photosensor is an electromagnetic sensor that responds to light and produces or converts it to an electrical signal which can be transmitted to a receiver for signal processing or other operations and ultimately read by an instrument or an observer. It may be capable of responding to or detecting any or all of the wavelengths of light that form the electromagnetic spectrum. Alternatively, the photosensor may be sensitive to a more restricted range of wavelengths.

An example of a photosensor which the visualization platforms described herein may include is a camera. A camera is a device used to capture images, either as still photographs or as sequences of moving images (movies or videos). A camera generally consists of an enclosed hollow with an opening (aperture) at one end for light to enter, and a recording or viewing surface for capturing the light at the other end. The recording surface can be chemical, as with film, or electronic. Cameras can have a lens positioned in front of the camera's opening to gather the incoming light and focus all or part of the image on the recording surface. The diameter of the aperture is often controlled by a diaphragm mechanism, but alternatively, where appropriate, cameras have a fixed-size aperture.

Exemplary electronic photosensors in accordance with the present disclosure include, but are not limited to, complementary metal-oxide-semiconductor (CMOS) sensors or charge-coupled device (CCD) sensors. Both types of sensors perform the function of capturing light and converting it into electrical signals. A CCD is an analog device. When light strikes the CCD it is held as a small electrical charge. The charges are converted to voltage one pixel at a time as they are read from the CCD. A CMOS chip is a type of active pixel sensor made using the CMOS semiconductor process. Electronic circuitry generally located next to each photosensor converts the received light energy into an electrical voltage and additional circuitry then converts the voltage to digital data which can be transmitted or recorded.

Exemplary image-guided systems suitable for implementing the system and practicing the methods described herein include the VERION® Image Guided System (Novartis AG Corporation, Basel, Switzerland) and the Zeiss CALLISTO Eye® (Carl Zeiss AG Corporation, Oberkochen, Germany), among other identifiable by skilled persons.

During the workflow of an image guided eye surgery, a pre-operative image of the eye is compared and aligned with an intraoperatively taken image. This alignment step is called registration and allows the placement of the treatment according to a treatment plan. Typically, the image guided system assists the surgeon during this registration step by providing a registration proposal, calculated using registration algorithms. Exemplary registration methods suitable for implementing the system and practicing the methods described herein include those used in the VERION® Image Guided System and such as those described in U.S. patent application Ser. No. 13/989,501 and U.S. patent application Ser. No. 14/065,173, which are incorporated herein by reference in their entirety.

For example, for refractive cataract surgery, the VERION Reference Unit performs key diagnostic measurements and captures a high resolution preoperative image of the patient's eye that includes scleral vessels, limbus and iris features—this serves as a "fingerprint" of the eye, and serves as a reference image to register and track the eye as a visual reference of surgical interventions, such as the positioning of incisions, capsulotomy and IOL positioning. Using the reference image as a fingerprint, the VERION® Digital Marker then allows surgeons to position all incisions and alignments in real time, during the surgical procedure.

Typically, for image-guided ophthalmic surgery, a registration step is performed wherein a pre-operative reference image of a patient's eye is aligned with an intra-operative image of the patient's eye. The alignment is performed to match the location of features of the pre-operative image of a patient's eye, such as scleral blood vessels, iris features, and limbus, with the location of the same features in the intra-operative image of the patient's eye. The registration step may include a rotation of the pre-operative image relative to the intra-operative image, which may be referred to as the registration angle. Various ophthalmic surgery systems employ computer processors that execute algorithms for performing the registration step that are identifiable by persons of ordinary skill in the art. The result of the registration step performed by the system may be referred to as a proposed registration, which includes a proposed registration angle.

During the image-guided surgery workflow, the surgeon needs to verify and confirm the registration proposal. This is done visually by verifying that the structures of the patient's eye match in both images, e.g. scleral vessels, iris features, and limbus, in the pre-operative reference image and the intra-operative image of the patient's eye.

Registration is required for every image guided surgery system that is based on pre-operative planning, e.g. the VERION® Image Guided System as well as the Zeiss CALLISTO Eye® system. Currently, image guided systems require the surgeon to verify and confirm the proposed registration according to various approaches. In one approach, the pre-operative reference image and the intra-operative image of the patient's eye are viewable by the ophthalmic surgeon on a screen where the two images are visualized as alternating images. In another approach, the pre-operative reference image and the intra-operative image of the patient's eye are shown next to each other. In another approach, the pre-operative and intra-operative images of the eyes are cut and unfolded or stretched to a rectangle and compared next to each other.

One problem with current approaches and systems for verification of the proposed registration is that manual intervention is often required to assess if proposed registration is representing the optimal registration angle. Typically, a thorough verification requires the surgeon to slightly change the proposed rotation in order to verify the proposed registration.

Advantages of the method and system described herein are expected to include easier and faster verification and confirmation of the proposed registration by the user, such as an ophthalmic surgeon.

In general, the method and system described herein provides an improved process and a system so configured for verification of a proposed registration during ophthalmic surgery. In various implementations, the method and system generally include a process to overlay or merge the pre-operative reference image and the intra-operative image, wherein both images are simultaneously viewable. Next, one of the images, such as the pre-operative reference image is caused to 'shake' in a rotational movement, e.g. by a few degrees back and forth, around the proposed registration angle. This 'shaking' could be triggered automatically or by an action of the user. Accordingly, the 'shaking' of one of the images in the merged image is expected to make it easier to differentiate between the structures and to verify the proposed registration, including verifying that the proposed registration angle is an optimal rotational registration of the images.

FIG. 1 shows a schematic 100 illustrating an exemplary method of the present disclosure. Schematic 100 shows a pre-operative (e.g., diagnostic) image 101 of an eye, showing features of the eye, such as blood vessels 102, a pupil 103, limbus 104, and sclera 105.

Schematic 100 also shows an intra-operative image 106 of an eye, showing eye clamps 107 (used to hold the eye open during ophthalmic surgery), and features of the eye, such as blood vessels 108, a pupil 109, limbus 110, and sclera 111.

Schematic 100 also shows an overlay of the pre-operative image 101 and the intra-operative image 106 to provide a merged image 112. Eye clamps 113 shown in the merged image 112 correspond to the eye clamps 107 in the pre-operative image 106. The merged image 112 shows overlaid features of the patient's eye, such as overlaid images of the limbus 116 corresponding to limbus 104 of the pre-operative reference image 101 and the limbus 110 of the intra-operative image 106. Also shown in the merged image 112 are other features of the eye, such as a sclera 119 in the merged image 112, corresponding to the overlaid images of the sclera 105 of the pre-operative image 101 and the sclera 111 of the intra-operative image 106, and blood vessels 115 in the merged image 112 corresponding to the overlaid images of the blood vessels 102 in the preoperative image 101 and the blood vessels 108 of the intraoperative image 106. The merged image 112 shows pupil 117 corresponding to pupil 103 of the pre-operative image 101 and pupil 118 corresponding to the pupil 109 of the intra-operative image 106.

It will be noted that, as shown in the exemplary schematic 101, the pupil 109 in the intra-operative image 106, which corresponds to the pupil 118 in the merged image 112 is dilated (larger) compared to the pupil 103 in the pre-operative image 101, which corresponds to the pupil 117 in the merged image 112. In some implementations, the size of the pupil 103/117 and the pupil 109/118 may be approximately the same size, or the pupil 103/117 may be smaller than the pupil 109/118.

The merged image 112 of FIG. 1 shows a center 114. In some implementations of the method and system described herein, the center 114 may correspond to the center of the limbus 116 of the overlaid image 112, or the center of the limbus 104 of the pre-operative reference image 101, or the center of the limbus 110 of the intra-operative image 106. It will be understood by persons skilled in the art, that the shape of the limbus 116/110/104 approximates a circle. In other implementations, the center 114 may correspond to the center of the pupil 103 of the pre-operative image 101 or the pupil 109 of the intra-operative image 106 shown respectively in the merged image 112 as pupil 117 and pupil 118. It will be understood by persons skilled in the art, that the shape of the pupil 103/109/117/118 approximates a circle.

In the merged image 112, transparency of the preoperative image 101 and/or the intraoperative image 106 may be set to a value greater than 0%. Accordingly, setting the transparency to a value greater than 0% for at least one of the preoperative image 101 and/or the intraoperative image 106 may allow a user to visualize the relative positions of the features of the eye in each of the preoperative image 101 and/or the intraoperative image 106 when overlaid in the merged image 112.

For example, the transparency of the preoperative image 101 and the intraoperative image 106 may be set to a value such as 50%. Other values may be used, identifiable by skilled persons to allow a user to visualize the relative positions of features of the eye in each of the preoperative image 101 and the intraoperative image 106 in the merged image 112. For example, when overlaid in the merged image 112, the transparency of the preoperative image 101 and/or the intraoperative image 106 may be set to a value between about 1-10%, 10-20%, 20-30%, 30-40%, 40-50%, 50-60-%, 70-80%, 80-90%, or 90-99%.

Arrow 120 and arrow 121 indicate the merging or overlaying of the preoperative image 101 and the intraoperative image 106 to provide the merged image 112. Skilled persons will understand that the terms "merging" and "overlaying" are approximately equivalent and as such are used interchangeably in the present description.

Arrow 122 indicates rotation of the preoperative image 101 relative to the intraoperative image 106 when overlaid as merged image 112. The center of rotation is center 114. It is understood that, in the merged image 112, rotation of the preoperative image 101 and/or the intraoperative image 106 may be performed, such that the angle of rotation of the preoperative image 101 is caused to vary in comparison to the intraoperative image 106.

The term "angle of rotation" as used herein refers to a value of an angle, typically measured in degrees (°), by which an image is rotated about a fixed point, such as the center of a circle. Conventionally, a counterclockwise rotation is considered a positive rotation and a clockwise rotation is considered a negative rotation, so that for instance a rotation of 310° (counter-clockwise) can also be called a rotation of −50° (clockwise) since 310°+50=360°, a full rotation).

Figure 2A:
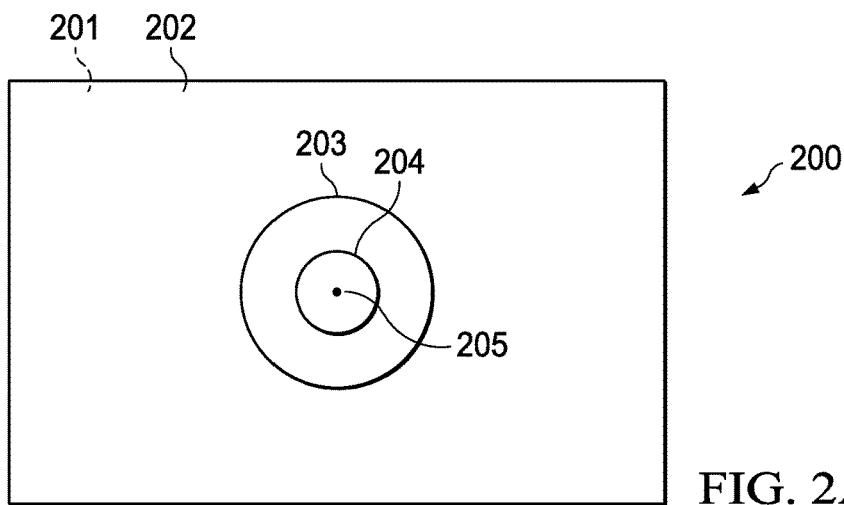
FIG. 2A is an exemplary schematic of the preoperative reference image overlaid on the intraoperative image.
Figure 2B:
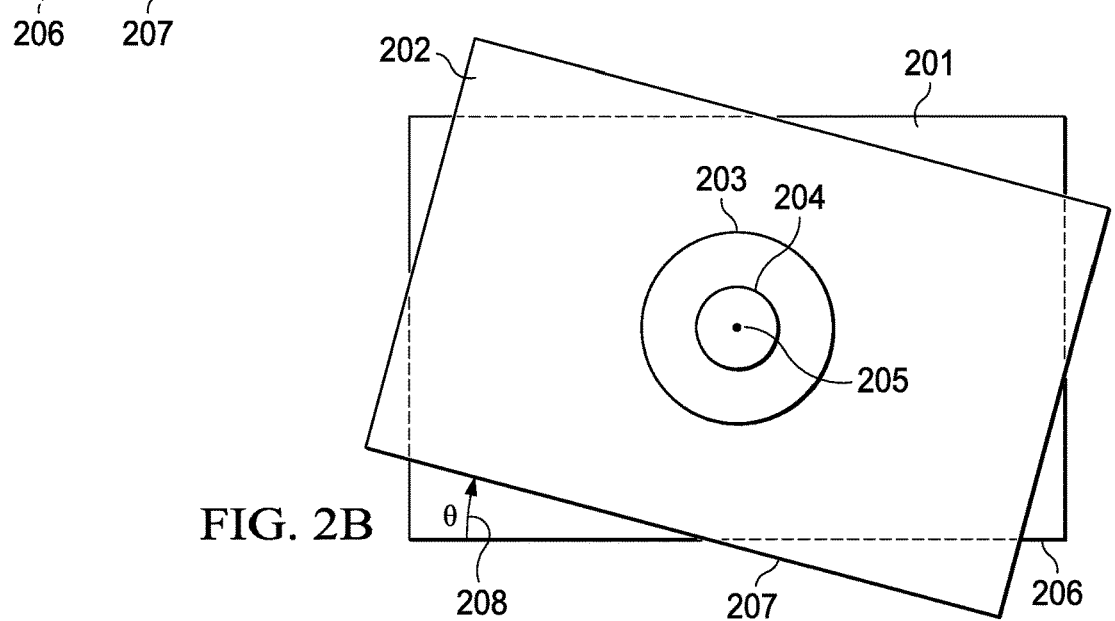
FIG. 2B is an exemplary schematic illustrating rotation of the preoperative reference image clockwise relative to the intraoperative image.
Figure 2C:
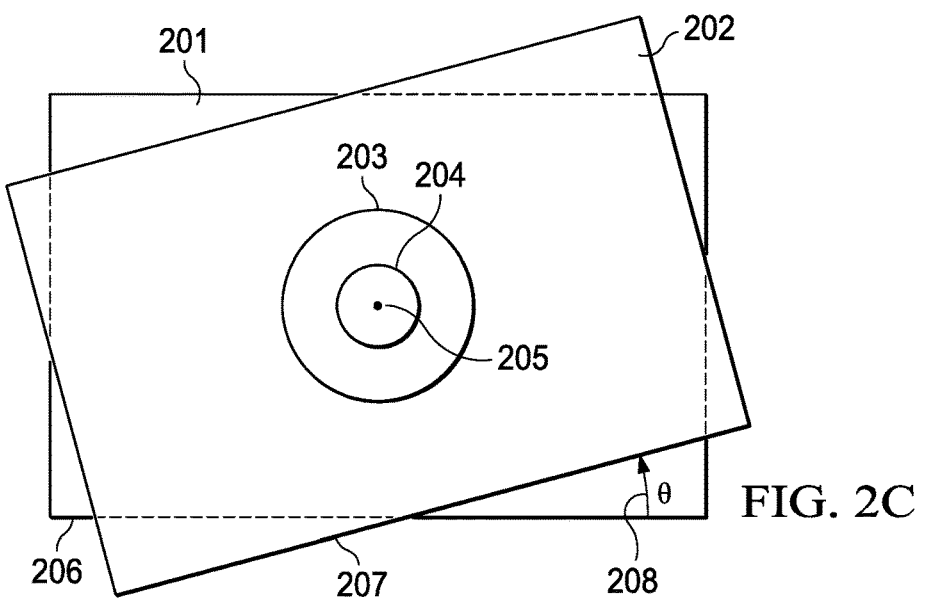
FIG. 2C is another an exemplary schematic illustrating rotation of the preoperative reference image anticlockwise relative to the intraoperative image.

FIGS. 2A-2C show exemplary schematics 200 of rotation of the preoperative image 101 relative to the intraoperative image 106 overlaid in merged image 112 of FIG. 1, depicted in FIG. 2A-2C respectively as preoperative image 201 and intraoperative image 202. As shown in FIG. 2A-2C, pupil 203 corresponds to the pupil 109/118 of the intraoperative image 106 of FIG. 1, and pupil 204 corresponds to the pupil 103/117 of the pre-operative image 101 of FIG. 1. A center 205 in FIG. 2A-2C corresponds to the center 114 of FIG. 1.

As shown schematically in FIG. 2A-2C, the term "angle of rotation" as used herein may refer, for example, to the rotational angle between a long side of the preoperative image 201 indicated as long side 206 and a long side of the intraoperative image 202, indicated as long side 207, for example when the preoperative image 201 and/or the intraoperative image 202 have a shape of landscape-oriented rectangles, as shown in FIG. 1 and FIGS. 2A-2C. Thus, for example, as shown in FIG. 2A, wherein the angle of rotation of the preoperative image 202 relative to the intraoperative image 201 is zero, the long sides 206 and 207 are parallel.

In particular, FIG. 2A shows an exemplary schematic of preoperative image 202 and intraoperative image 201 wherein the angle of rotation of preoperative image 202 relative to the intraoperative image 201 is zero (e.g., 0°).

In contrast to FIG. 2A, in exemplary FIG. 2B, the pre-operative image 201 is rotated about the center 205 in a clockwise direction, indicated by arrow 208, by a negative angle theta (θ) relative to the intraoperative image 202.

In exemplary FIG. 2C, the preoperative image 201 is rotated about the center 205 in an anti-clockwise direction, indicated by arrow 208, by a positive angle theta (θ) relative to the intraoperative image 202.

It will be understood by skilled persons that, during the registration process, the pre-operative reference image of a patient's eye may be rotated as required, according to the registration algorithm, to align the features of the pre-operative reference image with the intra-operative image of the patient's eye, to provide the proposed registration. The angle of rotation of the pre-operative reference image relative to the intra-operative image of the patient's eye during the registration process may be referred to as the registration angle. Accordingly, following the registration process, the proposed registration has a proposed registration angle.

Figure 3:
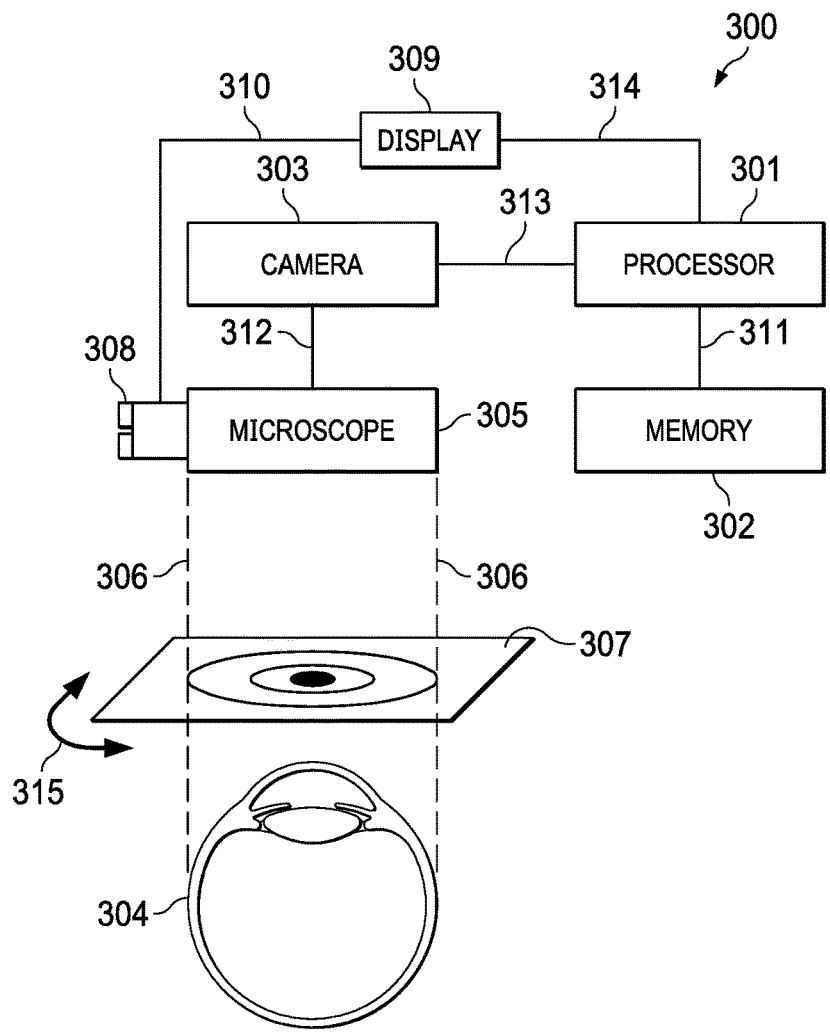
FIG. 3 is a schematic of an exemplary system for performing the method of verifying, by a user, a proposed registration during ophthalmic surgery.

The present disclosure provides a method and a system so configured for verifying, by a user, a proposed registration during ophthalmic surgery. FIG. 3 shows a schematic illustration of an exemplary system for performing the method of verifying, by a user, a proposed registration during ophthalmic surgery. The exemplary system shown in FIG. 3 includes a processor 301 and a non-transitory computer-readable medium, otherwise referred to herein as memory 302 that is accessible to the processor via a connection 311. The memory 302 contains instructions executable by the processor 301 for acquiring, from a photosensor, such as a camera 303, an intra-operative image of a patient's eye 304 under magnification by a microscope 305. The microscope 305 is shown connected to the camera 303 via connection 312 and the camera 303 is shown connected to the processor 301 via connection 313. Dashed lines 306 indicate an intra-operative field of view of the patient's eye 304 viewable through the microscope 305. The memory 302 also contains instructions executable by the processor 301 for retrieving, from a memory, a pre-operative reference image 307 of the patient's eye 304. The memory containing the pre-operative reference image 407 of the patient's eye 304 may be the same medium as memory 302 or it may be a different medium. For example, in some implementations, the memory 302 may be an internal computer hard disk drive, and the memory containing the pre-operative image of the patient's eye may be a removable medium such as a USB drive, among other configurations identifiable by skilled persons. The memory 302 has instructions executable by the processor 301 for performing a registration process to provide a proposed registration of the pre-operative reference image 307 of the patient's eye with respect to the intra-operative image of the patient's eye 304.

The processor 301 may include any suitable computer having an operating system such as those of UNIX or UNIX-like operating system, a Windows family operating system, or another suitable operating system. The non-transitory computer-readable medium 302 may encompass persistent and volatile media, fixed and removable media, and magnetic and semiconductor media, among others identifiable by persons of ordinary skill in the art. In addition, any suitable communication interface, including wired and/or wireless interfaces identifiable by skilled persons can be used as means for transmittal and receipt of electronic communication signals between the components of the system 300 described herein.

To perform the method described herein to verify the proposed registration, the system, such as the exemplary system shown in FIG. 3 is configured such that the memory 302 contains instructions executable by the processor 301 for overlaying the pre-operative reference image 307 and the intra-operative image of the patient's eye 304 to provide a merged image 112 as shown in FIG. 1, having the proposed registration, wherein the merged image is viewable by the user. In FIG. 3, the pre-operative reference image 307 is shown conceptually overlaid above the intra-operative patient's eye 304. In some implementations, the merged image may be viewable through microscope oculars 308. An exemplary system that includes this functionality is the VERION® Image Guided System, wherein a display 309 is integrated into the microscope, as indicated by line 310. Accordingly, in some implementations, the memory 302 may contain instructions executable by the processor 301 for displaying the viewable merged image via the oculars 308. In other implementations, the merged image may be viewable on a display 309, such as a separate display screen that is viewable without looking through the oculars 308. Accordingly, in some implementations, the memory 302 may contain instructions executable by the processor 301 for displaying the viewable merged image on the display 309. The memory 302 has instructions executable by the processor 301 for sending the merged image to the display 309 via connection 314.

The system is configured so that the memory 302 contains instructions executable by the processor 301 for adjusting the transparency of at least one of the pre-operative reference image and the intra-operative image, so that the pre-operative reference image and the intra-operative image are simultaneously viewable in the merged image on the display 309 by the user. Typically, in some implementations, the transparency of the pre-operative reference image will be adjusted. In some implementations, the memory 302 contains instructions executable by the processor 301 to adjust, for example increase, the transparency of at least one of the pre-operative reference image and the intra-operative image to at least about 1%, such as between about 1-10%, 10-20%, 20-30%, 30-40%, 40-50%, 50-60%, 60-70%, 80-90% or about 90-99%. In some implementations, the transparency is about 50%.

It will be understood that, typically upon merging two images, the merged image is said to have two layers, and one of the images may be said to be on top of the other. Accordingly, if only one of the pre-operative reference image and the intra-operative image are made transparent, then the image in the merged image that is on top (e.g. closest to the point of view of the user) will be made transparent, so that the image underneath (e.g. in the lower layer) will be viewable through the image on the top layer.

Algorithms for adjusting transparency of images that may be used in the system described herein are well known in the art, such as those used in widely used programs such as Photoshop® (Adobe Systems Incorporated, California).

In the system configured to perform the method of verifying the proposed registration, the memory 302 also contains instructions executable by the processor 301 for rotating the viewable pre-operative reference image 307 relative to the viewable intra-operative image of the patient's eye 304 in the viewable merged image having the proposed registration. It will be understood that the starting position for the rotation during the verification process in the merged image is the proposed registration angle of the proposed registration. As such, the proposed registration angle that is the starting position for the verification process may be considered as having a verification rotation of 0°, and angles of rotations indicated herein during the verification process are measured relative to the proposed registration angle. The rotation of the method of verifying the proposed registration is indicated in FIG. 3 by a double-headed arrow 315. As shown in FIGS. 1 and 2, for example the rotating may be centered on the center of the limbus or the pupil of the patient's eye in the pre-operative reference image. As would be understood by skilled persons, the limbus or the pupil forms an approximately circular shape having an identifiable center. With regard to the detection of magnified images of eyes and structures within eyes during ophthalmic surgery, the term "circle" as used herein refers to an approximately circular shape and may include ellipses and approximately elliptical shapes.

Accordingly, in some implementations the memory may contain instructions executable by the processor for determining the center of the image of the pupil 103/109/117/118 or the limbus 104/110/116 as shown in FIG. 1. For example, as described in U.S. patent application Ser. No. 14/065,173, herein incorporated by reference, the pupil center can be calculated using the center of gravity of a convex hull, or object segmented using intensity thresholding or alternatively, though transform or elliptical fit of the edge points, as would be understood by skilled persons. This list of methods is not exhaustive and other techniques identifiable by persons skilled in the art may be used. The limbus center can be calculated by utilizing the gradient in pixel intensity along a radial line from the pupil center. Using a predetermined gradient threshold, the edge points of the limbus can be found and an elliptical fit algorithm applied to find the limbus center. This list of methods is also not exhaustive and other techniques identifiable by persons skilled in the art may be used. In various implementations described herein, detection of the center of the approximately circular image of the limbus or the pupil may use any suitable algorithm identifiable by persons skilled in the art for detection of circles in images. Standard algorithms that may be used to detect circles include circle Hough Transform and random sample consensus (RANSAC), among others identifiable by skilled persons.

In some implementations, for the verification process, in the system the memory 302 contains instructions executable by the processor 301 to rotate the pre-operative reference image 307 of the patient's eye in relation to the intra-operative image of the patient's eye 304 clockwise and/or anticlockwise. In some implementations, the rotating may include at least one clockwise and at least one anticlockwise rotation and the clockwise rotation and the anticlockwise rotation alternates. The rotation or rotations may be repeated, for example up to about 20 times. In some implementations, the rotation is repeated about 10 times. In particular, in some implementations, the rotations may be alternated clockwise and anticlockwise. In some implementations, the alternations of clockwise and anticlockwise rotations may have a frequency of about 1-10 Hz (1-10 cycles per second), such as about 5 Hz. Each of the rotations may have an angle of rotation of about +/−1-10° relative to the proposed registration angle. For example, the angle of rotation may be about +/−5° relative to the proposed registration angle.

In some implementations, in the verification process, the rotating may include a series having a plurality of viewable alternating clockwise and anticlockwise rotations relative to the proposed registration angle, wherein the series has a first rotation having a first angle, and each successive viewable rotation of the series has a smaller angle relative to the proposed registration angle. For example, the plurality of viewable alternating clockwise and anticlockwise rotation angles may include about 10 alternating clockwise and anti-clockwise rotation angles, and the angle of each successive viewable rotation relative to the proposed registration angle may decrease by about 1°.

For example, such a series of alternating rotation angles may include the following, relative to the proposed registration angle: +10°, −9°, +8°, −7°, +6°, −5°, +4°, −3°, +2°, −1°, 0°.

Figure 4:
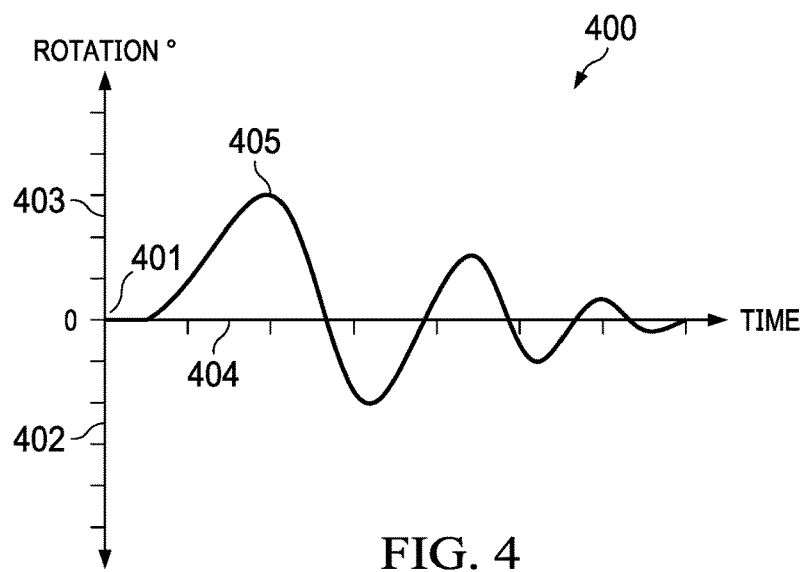
FIG. 4 is an exemplary schematic illustrating an exemplary relationship between rotation angle and time, wherein the rotation angle decreases over time in a series of alternating clockwise and anticlockwise rotations.

For example, in the verification process, FIG. 4 shows a schematic graph 400 illustrating an exemplary relationship between rotation angle and time, wherein the rotation angle decreases over time in a series of alternating clockwise and anticlockwise rotations. In particular, the graph 400 shows a vertical axis representing rotation angle (rotation °), which shows positive verification rotation angles (indicating anti-clockwise rotation angle relative to the proposed registration angle) and negative verification rotation angles (indicating clockwise rotation angle relative to the proposed registration angle). Accordingly, the point wherein the value of the verification rotation angle is zero (0°) at the origin of the graph, indicated by 401, represents the angle of the proposed registration, as described herein. Accordingly, the clockwise negative verification rotation values are shown along the portion of the axis below point 401, indicated by 402, and the anti-clockwise positive verification rotation values are shown along the portion of the axis above point 401, indicated by 403. The axis indicating time is indicated by 404. In FIG. 4, the exemplary graph 400 shows line 405 indicating a series of viewable alternating clockwise and anticlockwise rotations, wherein the series has a first rotation having a first angle, and each successive viewable rotation of the series has a smaller angle. In particular, at the left end of axis 404, line 405 is shown having a value of 0°, indicating the registration angle, followed by a series of verification rotation angles that peak with successively smaller values. Finally, at the right end of axis 404, line 405 is shown returning to a value of 0°.

Following the rotation or series of rotations in the verification process described herein, the proposed registration in the merged image may be viewable. Thus, following the verification process described herein, the processor 301 may execute instructions contained in the memory 302 to again present the merged image having the proposed registration on the display 309.

Following the verification process described herein, the user may confirm the proposed registration as an optimal registration, or the user may not confirm the proposed registration as an optimal registration. The verification process described herein may be performed as many times as required for the user to make a determination to either confirm or not confirm the proposed registration as an optimal registration. Accordingly, the system and method may further include one or more of the performing, overlaying, adjusting, and rotating steps.

Thus, in some implementations, following the performing of the registration process, the memory 302 may contain instructions executable by the processor 301 for initiating the overlaying, adjusting and rotating steps automatically. In other implementations, following the performing of the registration process, the user may initiate the system to perform the overlaying, adjusting, and rotating steps.

Accordingly, the system described herein is configured to allow a user to simultaneously view the pre-operative reference image and the intra-operative image in a merged image, wherein a registration process has been performed on the pre-operative reference image and the intra-operative image, and the merged image has a proposed registration.

Subsequently, during the verification process described herein, the proposed registration may be verified by the user. As described herein, the verification process described herein involves a method wherein the user views a computer processor-controlled temporary rotation of the pre-operative reference image away from the proposed registration angle.

The process herein described wherein, with regard to the proposed registration, the rotational angle of the pre-operative reference image of a patient's eye is momentarily varied from the rotational angle of the proposed registration may be referred to as "shaking" the pre-operative image relative to the proposed registration angle in the merged image. The shaking is performed to allow the user to verify the proposed registration.

During the verification process, in various implementations, the method and system allows the user to visualize the momentary variation of the rotation angle of the preoperative reference image relative to the intra-operative image of the patient's eye away from the proposed registration angle.

Various parameters of the verification process described herein may be customized according to user preference, such as the transparency, rotation angle, number of repetitions of rotation, and frequency of rotation. Accordingly, the exemplary system shown in FIG. 3 may additionally include a control panel (not shown), such as a touch screen, having user-operated controls or commands that allow a surgeon to adjust the parameters.

In some implementations, upon completion of the proposed registration, the verification process described herein may be initiated by the processor executing instructions contained in the memory. In other implementations, upon completion of the proposed registration, the user may initiate the steps of the verification process, e.g. by selecting a user-operated control to initiate the verification process, e.g. a command displayed on a control panel, such as a touch screen, the command configured to initiate the verification process in the system. In some implementations, the initiation of the verification may be selectable between initiation by the processor and initiation by the user. Accordingly, the control panel may include a user-operated controls or commands configured to effect, via instructions contained in the memory, the selection between initiation by the processor and initiation by the user. Accordingly, following the registration process, the verification process including the overlaying, adjusting, and rotating steps may be triggered automatically, or it may be triggered by the user. In general, it is understood that the term "automatically" refers to an action or a process that does not require manual control or manipulation by a user, such as an ophthalmic surgeon.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A system configured for verifying, by a user, a proposed registration during ophthalmic surgery, the system comprising:
   a processor; and
   a non-transitory computer-readable medium accessible to the processor containing instructions executable by the processor for:
   acquiring, from a photosensor, an intra-operative image of a patient's eye under magnification by a microscope;
   retrieving, from a non-transitory computer-readable medium, a pre-operative reference image of the patient's eye, wherein the limbus of the pre-operative image of the patient's eye has a center;
   performing a registration process to provide a proposed registration of the pre-operative reference image of the patient's eye and the intra-operative image of the patient's eye;
   overlaying the pre-operative reference image and the intra-operative image to provide a merged image having the proposed registration, wherein the merged image is viewable by the user;
   adjusting the transparency of at least one of the pre-operative reference image and the intra-operative image, so that the pre-operative reference image and the intra-operative image are simultaneously viewable in the merged image by the user; and
   rotating the viewable pre-operative reference image relative to the viewable intra-operative image comprised in the viewable merged image, wherein the rotating is centered on the center of the limbus of the patient's eye in the pre-operative reference image; wherein the rotating comprises a series of clockwise and anticlockwise rotations, each clockwise rotation followed by an anticlockwise rotation; wherein the series has a first viewable rotation having a first angle; and following the first viewable rotation, each successive viewable rotation of the series has a smaller angle;
   thereby allowing the user to verify a proposed registration during ophthalmic surgery.

2. The system of claim 1, wherein the transparency is selected from between about 1-10%, 10-20%, 20-30%, 30-40%, 40-50%, 50-60%, 60-70%, 70-80%, 80-90%, and 90-99%.

3. The system of claim 2, wherein the transparency is about 50%.

4. The system of claim 1, wherein the rotating is clockwise.

5. The system of claim 1, wherein the rotating is anti-clockwise.

6. The system of claim 1, wherein the rotation is repeated from about 1 to 20 times.

7. The system of claim 6, wherein the rotation is repeated with a frequency of between 1-10 Hz.

8. The system of claim 1, wherein the rotation has an angle between about 1°-10°.

9. The system of claim 8, wherein the angle is about 5°.

10. The system of claim 1, wherein the plurality of viewable rotations comprises about 10 rotations.

11. The system of claim 1, wherein the first angle is about 10°.

12. The system of claim 1, wherein the angle of each successive viewable rotation decreases by about 1°.

13. The system of claim 1, wherein following the series, the proposed registration is viewable.

14. The system of claim 1, further comprising one or more of the performing, overlaying, adjusting, and rotating steps.

15. The system of claim 1, wherein the microscope comprises oculars, and wherein the non-transitory computer-readable medium accessible to the processor contains instructions executable by the processor for displaying the viewable merged image via the oculars.

16. The system of claim 1, wherein the system further comprises a display;

and wherein the non-transitory computer-readable medium accessible to the processor contains instructions executable by the processor for displaying the viewable merged image on the display.

17. The system of claim 1, wherein the overlaying, adjusting, and rotating is initiated by the processor executing instructions contained in the non-transitory computer-readable medium.

18. The system of claim 1, wherein the overlaying, adjusting, and rotating is initiated by the user.

19. The system of claim 1 wherein the series comprises at least six alternating clockwise and anticlockwise rotations, each rotation having an angle of rotation wherein the angle of rotation of each successive alternating rotation is smaller than an immediately preceding angle of rotation.

20. The system of claim 1 wherein the series comprises alternating clockwise and anticlockwise rotations, each rotation having an angle of rotation that follows the series: +10°, −9°, +8°, −7°, +6°, −5°, +4°, −3°, +2°, −°, 0°.

* * * * *